United States Patent [19]

Takago

[11] 4,248,992

[45] Feb. 3, 1981

[54] GAUNIDYL-CONTAINING ORGANOSILICON COMPOUNDS

[75] Inventor: Toshio Takago, Annaka, Japan

[73] Assignee: Shin-Etsu Chemical Co. Ltd., Tokyo, Japan

[21] Appl. No.: 77,195

[22] Filed: Sep. 20, 1979

Related U.S. Application Data

[63] Continuation-in-part of Ser. No. 63,172, Aug. 3, 1979, abandoned, which is a continuation of Ser. No. 917,660, Jun. 21, 1978, Pat. No. 4,180,642.

[30] Foreign Application Priority Data

Jun. 29, 1977 [JP] Japan ................. 52-77590

[51] Int. Cl.$^3$ .............................................. C08G 77/04
[52] U.S. Cl. ................................... 528/28; 106/18.32; 556/424; 528/38; 424/184; 427/2; 427/387
[58] Field of Search ................. 260/448.2 N, 448.2 E; 528/28, 38; 424/184; 427/2, 387; 106/18.32; 556/424

[56] References Cited

U.S. PATENT DOCUMENTS

| | | | |
|---|---|---|---|
| 3,819,563 | 6/1974 | Takago et al. ................. | 528/901 |
| 4,020,044 | 4/1977 | Crossan et al. ................. | 528/901 |
| 4,180,642 | 12/1979 | Takago ................. | 528/32 |

*Primary Examiner*—Melvyn I. Marquis
*Attorney, Agent, or Firm*—Toren, McGeady and Stanger

[57] ABSTRACT

The invention provides a novel class of organosilicon compounds having in a molecule at least one monovalent guanidyl group represented by the general formula

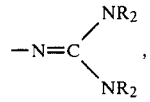

in which R is a hydrogen atom or a monovalent hydrocarbon group. Typical examples of the organosilicon compounds are 2-[3-(trimethoxysilyl)propyl]-1,1,3,3-tetramethylguanidine and 2-[3-(methyldimethoxysilyl)propyl]-1,1,3,3-tetramethylguanidine as well as the organopolysiloxanes as the hydrolysis-condensation products of these guanidyl-containing organosilanes.

The guanidyl-containing organosilicon compounds are readily synthesized by the dehydrohalogenation reaction between an organosilicon compound having in a molecule at least one halogen-substituted monovalent hydrocarbon group and a guanidine compound in the presence of an acid acceptor.

The guanidyl-containing organosilicon compounds are useful in preventing growth of microbial organisms, e.g. molds, on the surface of articles made of various rubbers and plastics, especially, silicone rubbers.

4 Claims, No Drawings

GAUNIDYL-CONTAINING ORGANOSILICON COMPOUNDS

BACKGROUND OF THE INVENTION

This is a continuation-in-part application of Ser. No. 063,172 copending application filed on Aug. 3, 1979, now abandoned which in turn is a continuation of the now allowed application Ser. No. 917,660 filed on June 21st, 1978 now U.S. Pat. No. 4,180,642.

The present invention relates to a novel class of organosilicon compounds having a guanidyl group in the molecule as well as to the method for the preparation and uses thereof.

The inventive organosilicon compounds have a substituted or unsubstituted guanidyl group represented by the general formula

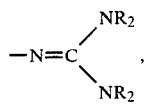

in which R denotes a hydrogen atom or a monovalent hydrocarbon group. Such a class of organosilicon compounds is hitherto unknown and described in none of the prior art literatures.

SUMMARY OF THE INVENTION

As is described above, an object of the present invention is to provide a novel and useful class of organosilicon compounds having a guanidyl group defined by the above general formula in the molecule.

Another object of the present invention is to provide a method for the preparation of the guanidyl-containing organosilicon compounds.

Further object of the present invention is to provide a novel use of the guanidyl-containing organosilicon compounds as an antifouling agent or antifungal agent in shaped articles of rubbers and plastics.

Thus, the inventive guanidyl-containing organosilicon compound is an organosilane compound having a substituted or unsubstituted guanidyl group bonded to the silicon atom through a divalent hydrocarbon group, preferably, an alkylene group, as represented by the general formula

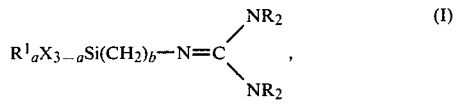

in which R has the meaning as defined above, $R^1$ is a hydrogen atom or a monovalent hydrocarbon group, X is a hydrolyzable atom or group, a is 0 or a positive integer of 1, 2 or 3, and b is a positive integer, preferably, in the range from 1 to 6 inclusive.

The above defined guanidyl-containing organosilane compound is readily prepared by the reaction of an organosilane compound having a halogen-substituted monovalent hydrocarbon, e.g. alkyl, group directly bonded to the silicon atom with guanidine or a substituted guanidine $(NR_2)_2C=NH$ in the presence of an acid acceptor.

A guanidyl-containing organopolysiloxane compound can also be readily obtained by the hydrolysis and condensation of the above guanidyl-containing organosilane compound having at least one hydrolyzable atom or group.

The guanidyl-containing organosilicon compounds are useful as a catalyst for the reaction between a hydroxy-terminated organopolysiloxane and a vinyloxy-containing organosilane compound and also as an antifouling agent or antifungal agent effectively preventing the growth of various microbial organisms such as molds on the surface of shaped articles of rubbers and plastics.

DETAILED DESCRIPTION OF THE PREFERRED EMBODIMENTS

As is described above, the guanidyl-containing organosilane compounds as a class of the inventive guanidyl-containing organosilicon compounds are represented by the above general formula (I). In the formula, R is a hydrogen atom or a monovalent hydrocarbon group such as alkyl groups, e.g. methyl, ethyl and propyl groups, aryl groups, e.g. phenyl and tolyl groups, aralkyl groups, e.g. benzyl group and alkenyl groups, e.g. vinyl and allyl groups as well as those groups derived from these hydrocarbon groups by substituting part or all of the hydrogen atoms therein with substituent groups or atoms such as halogen atoms and cyano groups. Among the above named hydrocarbon groups, methyl and ethyl groups are preferred by the reason of the easiness in the synthetic preparation. It is of course that all of the four atoms or groups expressed by R may be identical with each other or different from each other.

The symbol $R^1$ denotes a hydrogen atom or a monovalent hydrocarbon group similar to those denoted by R directly bonded to the silicon atoms, among which any one of the groups conventionally present in various ordinary organosilane compounds such as methyl, ethyl, phenyl and vinyl groups are suitable.

On the other hand, the symbol X denotes a hydrolyzable atom such as halogens, e.g. chlorine, or a hydrolyzable group bonded to the silicon atom such as alkoxy groups, e.g. methoxy and ethoxy groups, and acyloxy groups, e.g. acetoxy group, among which alkoxy groups such as methoxy and ethoxy groups are preferred also by the reason of easiness in the synthetic preparation.

The numbers of the atoms or groups expressed by $R^1$ and the atoms or groups expressed by X depend on the value of a in the formula which can be 0, 1, 2 or 3. As is mentioned above, the guanidyl-containing organosilane compounds must have at least one atom or group expressed by X with the value of a not equal to 3 in order that a guanidyl-containing organopolysiloxane compound is derived from the silane compound by hydrolysis into a silanol-containing compound followed by the silanol condensation reaction thereof.

As is shown by the general formula (I), the guanidyl group in the guanidyl-containing organosilane compounds of the invention is bonded to the silicon atom through an alkylene group expressed by the formula $-(CH_2)_b-$, in which b is a positive integer. In particular, b is limited to a number from 1 to 6 inclusive with preference of 3 only by the reason of easiness of the synthetic preparation.

Several of the examples of the inventive guanidyl-containing organosilane compounds are as follows, in which Me, Et, Pr and Ph stand for methyl, ethyl, propyl and phenyl groups, respectivley.

2-[3-(trimethylsilyl)propyl]-1,1,3,3,-tetramethylguanidine

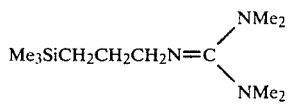

2-[3-(trimethoxysilyl)propyl]-1,1,3,3-tetramethylguanidine

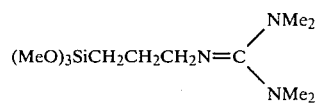

2-[3-(methyldimethoxysilyl)propyl]-1,1,3,3-tetramethylguanidine

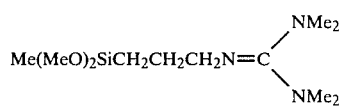

2-[3-(dimethylmethoxysilyl)propyl]-1,1,3,3-tetramethylguanidine

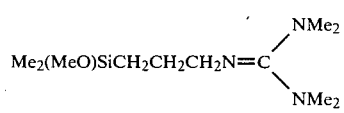

2-[3-(triethoxysilyl)propyl]-1,1,3,3-tetramethylguanidine

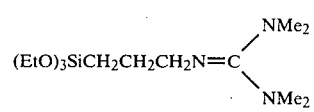

2-[3-(methyldimethoxysilyl)propyl]-1,1,3,3-tetraethylguanidine

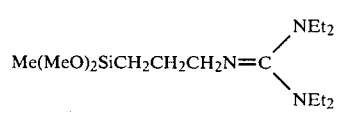

The above named guanidyl-containing organosilane compounds are readily synthesized by the dehydrohalogenation reaction of a halogenoalkyl-containing organosilane such as chloropropyltrimethoxysilane and guanidine or a substituted guanidine compound such as 1,1,3,3-tetramethylguanidine in the presence of an acceptor for the hydrogen halide. Being a basic compound, the guanidine or substituted guanidine compounds per se can serve as the acceptor for the hydrogen halide when used in an excess over the equivalent amount so as that the use of particular acid acceptor compound can be saved. The reaction is carried out usually in an inert solvent such as hydrocarbons, e.g. xylene, at an elevated temperature up to the refluxing temperature of the reaction mixture for a period of about a half to 5 hours. After completion of the reaction, the precipitated salt of the hydrogen halide and the acid acceptor is removed by filtration and the filtrate is subjected to distillation, if necessary, under reduced pressure to give the objective guanidyl-containing organosilane compound.

The derivation of a guanidyl-containing organopolysiloxane compound from one of the above named guanidyl-containing organosilane compounds having at least one hydrolyzable atom or group is rather an easy matter for those skilled in the art of silicones. For example, the above given 2-[3(dimethylmethoxysilyl)propyl]-1,1,3,3-tetramethylguanidine can be hydrolyzed and subjected to the silanol condensation reaction to give a guanidyl-containing disiloxane compound 1,3-bis(tetramethylguanidylpropyl)-1,1,3,3-tetramethyldisiloxane expressed by the formula:

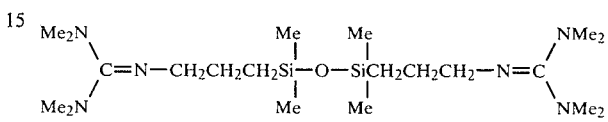

Similarly, cohydrolysis of a guanidyl-containing organosilane and an organosilane without the guanidyl group followed by co-condensation results in an organopolysiloxane composed of guanidyl bonded organosiloxane units without the guanidyl groups. An example of such an organopolysiloxane is 1-(tetramethylguandiylpropyl)-1,1,3,3,3-pentamethyldisiloxane expressed by the structural formula:

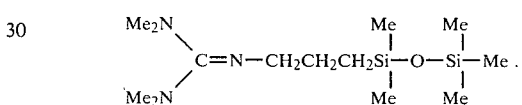

As has been disclosed in the parent application, the above described guanidyl-containing organosilicon compounds are useful as a catalyst for the reaction of silanol groups and silicon-bonded vinyloxy groups and curable organopolysiloxane compositions have been proposed in which the guanidyl-containing organosilicon compound is formulated as the crosslinking aid.

Seeking further application fields of the guanidyl-containing organosilicon compounds, the inventor unexpectedly discovered that the guanidyl-containing organosilicon compounds of the present invention are effective in preventing the growth of certain mold stocks belonging to the classes of aspergillus, penicillium, rhizopus and the like, especially, on the surfaces of shaped articles of rubbers and plastics when incorporated therein exhibiting an excellent anti-fouling or antifungal effect. In particular, the guanidyl-containing organosilicon compounds are effective as an antifungal agent in various silicone products such as silicone rubbers owing to the excellent affinity thereof with the silicones as well as the high thermal stability to withstand the elevated temperature at which the silicone products are cured. The amount of the guanidyl-containing organosilicon compound to be formulated in the articles of rubbers or plastics depends on the types of the rubbers or plastics but it may be in the range from 0.05 to 3 parts by weight per 100 parts by weight of the rubber or plastic.

Following are the examples to illustrate the inventive organosilicon compounds, the method for the preparation thereof and the effectiveness of the inventive organosilicon compounds in preventing the growth of microbial organisms on the surface of rubbers or plastics.

EXAMPLE 1.

Into a reaction vessel were introduced 483 g (4.2 moles) of 1,1,3,3-tetramethylguanidine and 50 g of xylene to dissolve the above guanidine compound and the reaction mixture was heated at 100° to 140° C. While maintaining the temperature in this range, 397 g (2.0 moles) of 3-chloropropyltrimethoxysilane was added dropwise into the reaction mixture under agitation and the reaction was continued for further 2 hours at 120° C. followed by cooling to room temperature. The hydrochloride of the guanidine compound precepitated in the reaction mixture was removed by filtration and the filtrate solution was subjected to distillation under reduced pressure to give 288 g of a liquid product boiling at 150.0° C. under a pressure of 10 mmHg.

This liquid product was subjected to elementary analysis, infrared absorption spectral analysis, NMR absorption spectral analysis and mass spectral analysis to give the results as shown below, from which the compound was identified to be 2-[3-(trimethoxysilyl)propyl]-1,1,3,3-tetramethylguanidine $C_{11}H_{27}O_3N_3Si$. The above given yield of the compound was about 52% of the theoretical based on the starting silane compound.

Elementary analysis:

|    | Found, % | Calculated, % as $C_{11}H_{27}O_3N_3Si$ |
|----|----------|------------------------------------------|
| Si | 10.19    | 10.11                                    |
| C  | 47.68    | 47.65                                    |
| H  | 9.71     | 9.75                                     |
| N  | 15.17    | 15.16                                    |

Infrared absorption spectral analysis:

| principal absorption bands appearing at | | |
|---|---|---|
| 1090 cm$^{-1}$ | assigned to | $\geq$Si—O—CH$_3$; |
| 1220 cm$^{-1}$ | assigned to | $\geq$Si—CH$_2$—; and |
| 1620 cm$^{-1}$ | assigned to | $>$C=N— |

NMR absorption spectral analysis:

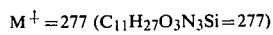

| a b c d | |
|---|---|
| | δ-value |
| a | 3.50 |
| b | 0.50 |
| c | 1.52 |
| d | 3.03 |
| e | 2.62 |

Gas-mass spectral analysis for molecular weight:

$M^+ = 277$ ($C_{11}H_{27}O_3N_3Si = 277$)

EXAMPLE 2.

Into a reaction vessel were introduced 380 g (3.3 moles) of 1,1,3,3-tetramethylguanidine and 40 g of xylene to dissolve the above guanidine compound and the reaction mixture was heated at 100° to 140° C. While maintaining the temperature in this range, 274 g (1.5 moles) of 3-chloropropylmethyldimethoxysilane was added dropwise to the reaction mixture under agitation and the reaction was continued for further 2 hours at 120° C. followed by cooling to room temperature. The hydrochloride of the guanidine compound precipitated in the reaction mixture was removed by filtration and the filtrate solution was subjected to distillation under reduced pressure to give 188 g of a liquid product boiling at 115.0° C. under a pressure of 5 mmHg.

The liquid product was subjected to the same analysis as in Example 1 to give the results below, from which the compound was identified to be 2-[3-(methyldimethoxysilyl)-propyl]-1,1,3,3-tetramethylguanidine $C_{11}H_{27}O_2N_3Si$. The above given yield of the product was about 48% of the theoretical based on the starting silane compound.

Elementary analysis:

|    | Found, % | Calculate, % as $C_{11}H_{27}O_2N_3Si$ |
|----|----------|------------------------------------------|
| Si | 10.76    | 10.73                                    |
| C  | 50.60    | 50.57                                    |
| H  | 10.32    | 10.34                                    |
| N  | 16.11    | 16.09                                    |

Infrared absorption spectral analysis:

| principal absorption bands appearing at | | |
|---|---|---|
| 1090 cm$^{-1}$ | assigned to | $\geq$Si—O—CH$_3$; |
| 1250 cm$^{-1}$ | assigned to | $\geq$Si—CH$_3$; and |
| 1620 cm$^{-1}$ | assigned to | $>$C=N— |

NMR absorption spectral analysis:

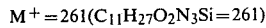

| a b c d e | |
|---|---|
| | δ-value |
| a | 3.50 |
| b | 0.00 |
| c | 0.50 |
| d | 1.52 |
| e | 3.03 |
| f | 2.62 |

Gas-mass spectral analysis for molecular weight:

$M^+ = 261$($C_{11}H_{27}O_2N_3Si = 261$)

EXAMPLE 3.

A commercially available heat-curable silicone rubber composition (KE-151, a product of Shin-Etsu Chemical Co., Japan) was admixed with 1.0% by weight of 2-[3-(trimethoxy-silyl)propyl]-1,1,3,3-tetramethylguanidine prepared in Example 1 and, after being uniformly blended, the composition was fabricated into sheets of 2 mm thickness by curing at 180° C.

for 10 minutes under pressure. For comparison, the same silicone rubber composition was fabricated into sheets without the addition of the guanidyl-containing organosilane compound in the same manner as above. The mechanical properties were substantially the same for these cured silicone rubber sheets with or without the addition of the guanidyl-containing organosilane compound.

The antifungal effect was examined with these cured rubber sheets by the cultivation test specified in JIS Z 2911 by use of three kinds of mold stocks, viz. *Aspergillus niger* ATCC 6275, *Penicillium citrinum* ATCC 9849 and *Rhizopus nigricans* SN 32 to find that no growth of the mold stocks was observed in the rubber sheets with admixture of the guanidyl-containing organosilane compound while the surface of the rubber sheets without the addition of the silane compound was found to be covered by the molds.

What is claimed is:

1. A shaped article of a rubber or plastic comprising from 0.05 to 3% by weight of an organosilicon compound having in a molecule at least one monovalent guanidyl group represented by the general formula

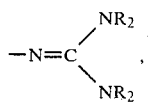

wherein R is a hydrogen atom or monovalent hydrocarbon group, said guanidyl group being bonded to the silicon atom of the organosilicon compound by a divalent hydrocarbon group.

2. A method for preventing growth of microbial organisms on the surface of a shaped article of a rubber or plastic which comprises adding from 0.05 to 3% by weight of an organosilicon compound having in a molecule at least one guanidyl group represented by the general formula

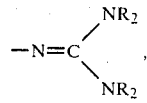

wherein R is a hydrogen atom or a monovalent hydrocarbon group, said guanidyl group being bonded to the silicon atom of the organosilicon compound by a divalent hydrocarbon group, to the rubber or plastic before the rubber or plastic is shaped.

3. A method for the preparation of an organosilicon compound having in a molecule at least one guanidyl group represented by the general formula

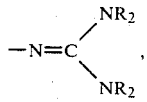

wherein R is a hydrogen atom or a monovalent hydrocarbon group, said guanidyl group being bonded to the silicon atom of the organosilicon compound by a divalent hydrocarbon group, which comprises reacting an organosilicon compound having in a molecule at least one halogen-substituted monovalent hydrocarbon group with a guanidine compound represented by the general formula $(NR_2)_2C=NH$, wherein R has the same meaning as defined above, in the presence of an acid acceptor.

4. The method as claimed in claim 3 wherein the acid acceptor is the guanidine compound present in excess over the equivalent amount to the organosilicon compound having in a molecule at least one halogen-substituted monovalent hydrocarbon group.

* * * * *

UNITED STATES PATENT OFFICE
CERTIFICATE OF CORRECTION

Patent No. 4,248,992            Dated February 3, 1981

Inventor(s) Toshio Takago

It is certified that error appears in the above-identified patent and that said Letters Patent are hereby corrected as shown below:

In the heading space of the patnet [63], should read as follows:

[63]  Continuation-in-part of Ser.No. 63,172, Aug.3,1979, Pat.No. 4,248,993, which is a continuation of Ser.No. 917,660, Jun.21,1978, Pat.No. 4,180,642.

Signed and Sealed this

Seventeenth Day of November 1981

[SEAL]

*Attest:*

*Attesting Officer*

GERALD J. MOSSINGHOFF

*Commissioner of Patents and Trademarks*